(12) United States Patent
Baillie et al.

(10) Patent No.: US 8,628,805 B2
(45) Date of Patent: Jan. 14, 2014

(54) STABILIZED COMPOSITION COMPRISING AT LEAST ONE ADRENERGIC COMPOUND

(75) Inventors: Alan J. Baillie, Helensburgh (GB); Kenneth MacDonald, Glasgow (GB); Pamela Porteous, Irvine (GB); Simon Hendry, Whiltshire (GB)

(73) Assignee: ALK AG, Volketswil (CH)

( * ) Notice: Subject to any disclaimer, the term of this patent is extended or adjusted under 35 U.S.C. 154(b) by 116 days.

(21) Appl. No.: 12/794,163

(22) Filed: Jun. 4, 2010

(65) Prior Publication Data
US 2011/0003015 A1 Jan. 6, 2011

Related U.S. Application Data (60) Provisional application No. 61/184,066, filed on Jun. 4, 2009.

(51) Int. Cl.
*A01N 59/02* (2006.01)
*A61K 33/04* (2006.01)

(52) U.S. Cl.
USPC .......................................... 424/711; 514/653

(58) Field of Classification Search
None
See application file for complete search history.

(56) References Cited

U.S. PATENT DOCUMENTS

| | | | |
|---|---|---|---|
| 3,149,035 A | 9/1964 | Riegelman | |
| 3,966,905 A | 6/1976 | Nite | |
| 4,734,438 A | 3/1988 | Macri | |
| 6,077,545 A | 6/2000 | Roskos et al. | |
| 6,224,883 B1 | 5/2001 | Roskos et al. | |
| 2003/0216413 A1 * | 11/2003 | Root-Bernstein et al. | 514/263.31 |
| 2005/0228336 A1 | 10/2005 | Keusch et al. | |
| 2008/0269347 A1 | 10/2008 | Bruss et al. | |
| 2012/0129944 A1 | 5/2012 | Baillie et al. | |

FOREIGN PATENT DOCUMENTS

| | | |
|---|---|---|
| CA | 981182 | 1/1976 |
| DE | 150694 A1 | 9/1981 |
| GB | 425678 | 3/1935 |
| GB | 930452 | 7/1963 |
| JP | 6298640 A | 10/1994 |
| WO | 9413274 | 6/1994 |
| WO | 9820869 | 5/1998 |

OTHER PUBLICATIONS

Grubstein B et al., "Stabilization of Epinephrine in a Local Anesthetic Injectable Solution Using Reduced Levels of Sodium Metabisulfite and EDTA", Drug Development and Industrial Pharmacy, 18(14), 1549-1566 (1992).
Third Party Submission Under 37 CFR 1.290, filed in U.S. Appl. No. 13/376,021 and mailed by USPTO on Nov. 29, 2012 (16 pages).
Portman et al., "Reaction Kinetics of Some Catecholamines Sodium Bisulfite Solutions", Drug Development and Industrial Pharmacy, 4(1), pp. 31-52 (1978).
Epipen Prescribing Information, Dec. 2000 (10 pages).
Restriction requirement mailed Jan. 25, 2013 for U.S. Appl. No. 13/376,021.
Wollman, H., and Raether, G., Examination of the Efficiency of Stabilizing Agents in Epinephrine Model Solution, Pharmacy, 38(1) 37-42 (1983), including English translation.
Third Party Submission under 37 CFR 1.290, filed in U.S. Appl. No. 13/376,021 on Mar. 28, 2013 (8 pages).

* cited by examiner

*Primary Examiner* — Sue Liu
*Assistant Examiner* — Daniel L Branson
(74) *Attorney, Agent, or Firm* — Fish & Richardson P.C.

(57) ABSTRACT

A stabilized composition comprising at least one adrenergic compound and at least one antioxidant selected from the group consisting of a bisulfate, a metabisulfite and a sulfite compound.

16 Claims, 5 Drawing Sheets

STABILIZED COMPOSITION COMPRISING AT LEAST ONE ADRENERGIC COMPOUND

FIELD OF THE INVENTION

The present invention relates to a stabilised composition having a significantly improved shelf-life stability with a substantially reduced susceptibility of light induced, thermal and oxidative degradation. More particularly the present invention relates to a stabilised composition comprising at least one adrenergic compound and at least one antioxidant selected from the group consisting of a bisulfate, a metabisulfate and a sulfite compound.

BACKGROUND OF THE INVENTION

Solutions of adrenergic compounds, in particular epinephrine and modifications thereof, find wide application for medicinal purposes. Epinephrine is one of the neural hormones responsible for the regulation of the heart, blood pressure, airway resistance, and energy metabolism. Epinephrine generates an inotropic effect, wherein it increases the heart rate, the force of contraction of the heart, narrows the blood vessels thus increasing blood pressure, reduces airway resistance to make it easier to breathe, and raises blood glucose and blood fatty acids to supply the body energy during stress. Its uses include at least combating low blood pressure during hemorrhagic, allergic or anaphylactic shock; opening the airways during asthmatic attack; restricting the distribution of locally administered drugs such as local anaesthetics; reducing nasal congestion; and/or performance aid in emergency situations.

Catechol compounds such as epinephrine are sensitive to oxidation to o-quinones, which can react further to form highly coloured compounds. Epinephrine can thus react to form adrenochrome, a highly coloured indole derivative. The rate of this reaction increases with pH, temperature and by the presence of metal ions, such as aluminium from various rubbers and iron from amber glassware. Epinephrine solutions may also lose potency as a result of racemisation and protection from light minimises this form of instability.

The modification or degradation of the catechol amines is undesirable for a number of reasons. Modification of the catechol amine results in loss of titer of the active ingredient, formation of compounds which may have undesirable physiological effects, and the appearance of a dark colour, which makes the solution offensive and unmarketable. The initial loss of active compound due to auto-oxidation during the preparation and packaging of such a solution is substantial despite the fact that such procedures are carried out as nearly as practically possible in an inert atmosphere and such a solution must be stored under refrigeration in order to decrease the rate of deterioration of the compound and thus prolong its shelf-life.

It is standard practice, in order to stabilise adrenergic compounds such as catechol amines against auto-oxidation, to combine therewith an antioxidant. Various antioxidants which have been used to stabilise catechol amine solution in a variety of formulations such as aerosols, eye-drops, injections etc, include: metabisulfite, bisulfate, sulfite, ascorbic acid, thiglycollate, thioglycerol, cysteine, propyl gallate and formaldehyde sulfoxylate.

A commercially available epinephrine formulation is the Epipen® formulation. The composition of the Epipen® formulation, designed to deliver a minimum of 0.3 g epinephrine in a 0.3 ml injection volume, is as follows:

| | |
|---|---|
| Epinephrine | 1.1 mg |
| Sodium chloride | 6.0 mg |
| Sodium metabisulfite | 1.7 mg |
| Hydrochloric acid | to pH 3.4 |
| Water for injection | to 1 ml |

GB 425,678 discloses a process for producing a substantially stable anesthetic solution for local anesthesia containing an acid salt of an anesthetic, epinephrine or a physiological equivalent normally requiring an acid to keep it stable and an antioxidant, which comprises adjusting the pH value of the solution by a buffer so that the solution has a pH value within a range from approximately 5.7 up to approximately neutral. Sodium bisulfite is mentioned as antioxidant.

GB 930,452 and U.S. Pat. No. 3,149,035 disclose stable pharmaceutical solutions of a catechol amine comprising an aqueous solution of the catechol amine together with oxine, boric acid, and sodium bisulfite, said solutions having a pH of 6.5-6.8.

U.S. Pat. No. 3,966,905 discloses stabilised catechol amine solutions comprising a catechol amine, a polyvinylpyrrolidone, borate and a physiologically acceptable antioxidant selected from the group consisting of ascorbic acid, erythorbic acid, acetylcysteine, and thioglycerol, at a substantially neutral or mildly basic pH.

CA 981182 discloses the stabilisation of I-epinephrine in a local anesthetic solution by using a combination of three specific antioxidants, i.e. bisulfite, ascorbic acid and thioglycerol, said solution comprising a local anesthetic selected from mepivacaine, bupivacaine and lidocaine, I-epinephrine, bisulfite, ascorbic acid and thioglycerol, and wherein said solution is of a pH of approximately 4.

US 2008/0269347 A1 discloses epinephrine formulations comprising epinephrine, EDTA, and at last one antioxidant, wherein the antioxidant is selected from the group consisting of cysteine, citric acid, thioglycerol, acetylcysteine, and a combination thereof.

DD-A1-150 694 discloses a formulation containing epinephrine hydrogen tartrate and sodium metabisulfite.

WO 94/13274 discloses formulations containing dobutamine hydrochloride and sodium metabisulfite.

WO 97/16196 discloses a formulation containing epinephrine and sodium metabisulfite.

WO98/20869 discloses a formulation containing epinephrine and sodium metabisulfite.

U.S. Pat. No. 4,734,438 discloses a formulation containing norepinephrine and sodium bisulfite.

There remains a need for a stabilised composition having an improved shelf-life stability with a substantially reduced susceptibility of light induced, thermal and oxidative degradation.

OBJECT OF THE INVENTION

It is an object of embodiments of the invention to provide a pharmaceutical composition comprising an adrenergic compound having improved stability and consequently enhanced shelf-life.

SUMMARY OF THE INVENTION

It has been found by the present inventor(s) that an improved stability, in particular stability against auto-oxidation and thermal stability, may be obtained through the use of at least one antioxidant selected from the group consisting of a bisulfite, a metabisulfite, or a sulfite compound, wherein the molar ratio of the adrenergic compound to the at least one antioxidant and the pH are in a specified range.

So, in a first aspect the present invention relates to a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

The invention is based on the surprising experimental finding that the stability of adrenaline is enhanced in the adrenaline/sulfite ratio range of 1.31-2.20 compared to the ratios used in conventional commercial products and other prior art formulations.

In a second aspect the present invention relates to a method for stabilising a liquid pharmaceutical composition comprising an adrenergic compound, comprising the steps of i) providing a solution of an adrenergic compound, ii) adding at least one antioxidant selected from the group consisting of a bisulfite, a metabisulfite, and a sulfite compound, iii) adjusting the pH thereof to a value in the range 2.0-5.0 optionally by addition of an acid or a base, wherein the molar ratio of the adrenergic compound to the at least one antioxidant, measured as sulfite-equivalents, is in the range 1.31-2.20.

In a third aspect the present invention relates to a use of at least one antioxidant selected from the group consisting of a bisulfite, a metabisulfite, and a sulfite compound for the stabilisation of a liquid pharmaceutical composition comprising an adrenergic compound, wherein the molar ratio of the adrenergic compound to the at least one antioxidant, measured as sulfite-equivalents, is in the range 1.31-2.20, and wherein the pH of said liquid composition is in the range of about 2.0-5.0.

In a fourth aspect the present invention relates to a kit comprising:
  i) a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0 and
  ii) an administration device.

In a fifth aspect the present invention relates to a method of improving at least one symptom of a medical condition requiring an adrenergic compound in an individual in need thereof, comprising administering to the individual a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

In a sixth aspect the present invention relates to a method of treating anaphylaxis in an individual comprising administering to the individual a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

In a seventh aspect the present invention relates to a liquid pharmaceutical composition for use in improving at least one symptom of a medical condition requiring an adrenergic compound in an individual in need thereof, comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

In an eighth aspect the present invention relates to a use of a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0, for the manufacture of a medicament for treating anaphylaxis in an individual.

DEFINITIONS

The expression "adrenergic compound" means any compound capable of stimulating the adrenergic nerves with the same or a similar effect as epinephrine. The mechanism of action of adrenergic compounds for use according to the present invention is direct-acting by interaction with specific receptors, and are classified as adrenergic receptor agonists stimulating α- and β-adrenergic receptors or as dopaminergic agonists stimulating the D1 receptor.

The expression "epinephrine" refers to (R)-4-(1-hydroxy-2-(methylamino)ethyl)benzene-1,2-diol and is used interchangeably with the expression "adrenaline".

The expression "antioxidant" refers to a substance capable of slowing or preventing the oxidation of other substances. Oxidation reactions can produce free radicals, which start chain reactions that may be damaging. Antioxidants terminate these chain reactions by removing free radical intermediates, and inhibit other oxidation reactions by being oxidized themselves.

The expression "a bisulfite" means any salt comprising the anion $HSO_3^-$.

The expression "a metabisulfite" means any salt comprising the anion $S_2O_5^{2-}$.

The expression "a sulfite" means any salt comprising the anion $SO_3^{2-}$.

The expression "sulfite equivalents" means the molar equivalent of sulfite ions generated through the use of a bisulfite, metabisulfite or sulfite salt. Thus a bisulfite or metabisulfite salt generates 2 sulfite equivalents per molecule of the respective compound, whereas a sulfite salt generates 1 sulfite equivalent per molecule of sulfite salt.

The expression "auto-injector" refers to an injection apparatus or device comprising an automatic needle deployment mechanism, which may be activated by hand by the user of the auto-injector.

The expression "ampoule" refers to a small sealed glass vial made to contain a pharmaceutical composition.

DETAILED DISCLOSURE OF THE INVENTION

Pharmaceutical Composition

The liquid pharmaceutical composition according to the invention comprises an adrenergic compound as defined above and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

The present invention provides an enhanced stability and thus shelf-life of the pharmaceutical composition with the use of a lower level of antioxidant than the current commercially available Epipen® formulation as compared to the level of adrenaline.

The pharmaceutical composition of the invention is particularly advantageous for applications, wherein it is not possible or highly impractical to keep the composition refrigerated, e.g. for precautionary emergency uses, where the user carries with him or her the composition always in all types of climates in order to allow for immediate administration in case of an emergency, such as an anaphylactic chock. An additional advantage of the pharmaceutical composition of the present invention is that it allows for a reduced level of antioxidant. In particular, this is an advantage, as some patients are in fact hypersensitive to high levels of bisulfite-, metasulfite- and sulfite-based antioxidants.

Specific examples of adrenergic receptor agonists include, but are not limited to: epinephrine, norepinephrine, phenylephrine, α-methylnorepinephrine, dopamine, albuterol, dobutamine, methoxamine, xylometazoline, oxymetazoline, clenbuterol, dexmedetomidine, mivazerol, methyldopa, clonidine, prenalterol, isoproterenol, fenoterol, metaproterenol, terbutaline, ritodrine, xamoterol, salbutamol, salmeterol, and zinterol. A specific example of a dopaminergic agonist includes, but is not limited to, fenoldopam.

In an embodiment of the present invention the adrenergic compound is selected from the group consisting of epinephrine, norepinephrine, phenylephrine, α-methylnorepinephrine, dopamine, methoxamine, clonidine, dobutamine, prenalterol, isoproterenol, fenoterol, albuterol, terbutaline, and metaproterenol, and physiologically acceptable salts thereof.

In an embodiment of the present invention the adrenergic compound is selected from the group of catecholamines consisting of epinephrine, norepinephrine, isoproterenol, and dopamine and physiologically acceptable salts thereof.

In an embodiment of the present invention the adrenergic compound is epinephrine or a physiologically acceptable salt thereof.

As non-limiting examples of physiologically acceptable salts may be mentioned addition salts of inorganic or organic acids, such as hydrochloric acid, hydrobromic acid, phosphoric acid, sulphuric acid, citric acid, tartaric acid, lactic acid, formic acid, and mucic acid.

It will be understood that as used throughout this specification the term bisulfite and metabisulfite means bisulfite ion ($HSO_3^-$) and metabisulfite ion ($S_2O_5^{2-}$), respectively, derivable from any pharmaceutically acceptable source or precursor, such source or precursor being illustrated, without limiting the foregoing, by ammonium, alkali-metal, alkaline earth metal, and amine salts and mixed salts of an alkali metal and an organic compound. Alkaline metals salts include salts of sodium and potassium, alkaline earth metal salts include calcium, magnesium, strontium and barium salts, and amine salts include salts of an amine, wherein the amine is a primary, secondary or tertiary lower-alkylamine such as methylamine, ethylamine, isopropylamine, n-butylamine, diethylamine, triethylamine and the like. Non-limiting examples of bisulfite and metabisulfite salts include salts such as sodium bisulfite ($NaHSO_3$) and sodium metabisulfite ($Na_2S_2O_5$), and acetone alkali-metal bisulfite such as acetone sodium bisulfite [$(CH_3)_2 C(OH)OSO_3Na$].

In an embodiment of the present invention the at least one antioxidant is sodium bisulfite or sodium metabisulfite.

In an embodiment of the present invention the at least one antioxidant is sodium metabisulfite.

In an embodiment of the present invention the molar ratio of the at least one adrenergic compound to the at least one antioxidant is in the range of 1.31 to 2.00.

In an embodiment of the present invention the molar ratio of the at least one adrenergic compound to the at least one antioxidant is in the range of 1.31-1.80.

In an embodiment of the present invention the molar ratio of the at least one adrenergic compound to the at least one antioxidant is in the range of preferably 1.31-1.60.

In an embodiment of the present invention the molar ratio of the at least one adrenergic compound to the at least one antioxidant is in the range of 1.31-1.50.

In an embodiment of the present invention the molar ratio of the at least one adrenergic compound to the at least one antioxidant is in the range of 1.31 to 1.40.

In an embodiment of the present invention the pH of the pharmaceutical composition is in the range of 2.5-4.5, preferably 3.0-4.0, more preferably 3.1-3.7 and most preferably 3.2 to 3.6.

In an embodiment of the present invention the pH is in the range of 3.3-3.5, more preferably about 3.4.

Adrenergic compounds, in particular epinephrine, are susceptible to degradation by auto-oxidation involving the formation of adrenaline-o-quinone, which in turn converts to adrenochrome. The rate of this reaction increases with pH and it has been found that the pH for maximum stability of epinephrine in solution is about 3.4.

Furthermore bisulfite and metabisulfite themselves contribute to the deterioration of adrenergic compounds independently of the auto-oxidative process since they react therewith to form a biologically inactive sulfonic acid derivative. According to the present invention, it has been shown that the rate of formation thereof is dependent on the molar ratio of adrenergic compound to antioxidant, a high ratio tending to suppress the formation. In accordance with the present invention, the optimum ratio of adrenergic compound and antioxidant is thus a carefully chosen balance between different influences.

An embodiment of the present invention is a pharmaceutical composition comprising:

| | |
|---|---|
| Epinephrine acid tartrate | 2.0 mg/ml |
| Sodium chloride | 6.0 mg/ml |
| Sodium metabisulfite | 0.57 mg/ml |
| HCl/NaoH | q.s. pH 3.4 |
| Water for injection | q.s. 1.0 ml |

In an embodiment of the present invention the pharmaceutical composition furthermore comprises one or more excipients or additives. Non-limiting examples thereof include osmolality-adjusting agents, pH-adjusting agents, chelating agents such as EDTA (ethylene-diamine-tetraacetic acid), carriers, etc.

Method of Stabilising a Pharmaceutical Composition

An embodiment of the present invention is a method for stabilising a liquid pharmaceutical composition comprising an adrenergic compound, comprising the steps of i) providing a solution of an adrenergic compound, ii) adding at least one antioxidant selected from the group consisting of a bisulfite, a metabisulfite, and a sulfite compound, iii) adjusting the pH thereof to a value in the range 2.0-5.0 optionally by addition of an acid or a base, wherein the molar ratio of the adrenergic compound to the at least one antioxidant, measured as sulfite-equivalents, is in the range 1.31-2.20.

Use of an Antioxidant for Stabilisation

An embodiment of the present invention is a use of at least one antioxidant selected from the group consisting of a bisulfite, a metabisulfite, and a sulfite compound for the stabilisation of a liquid pharmaceutical composition comprising an adrenergic compound, wherein the molar ratio of the adrenergic compound to the at least one antioxidant, measured as sulfite-equivalents, is in the range 1.31-2.20, and wherein the pH of said liquid composition is in the range of about 2.0-5.0.

Devices Containing the Pharmaceutical Composition

The present invention provides a kit comprising:
iii) a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0, and
iv) an administration device.

In an embodiment of the invention the administration device is an ampoule or an auto-injector.

In specific embodiments, the auto-injector delivers a single dose. In other specific embodiments part or all of the auto-injector is disposable and/or portable. An auto-injector may be supplied separately from the pharmaceutical composition, in alternative embodiments. The auto-injector, or any injection device, may comprise an exchangeable vessel for replacing the pharmaceutical composition, such as an insert, cartridge, vial etc. Such an exchangeable vessel may be glass or plastic, for example. An auto-injector comprises a volume of the pharmaceutical composition to be injected. In general, such injectors include a reservoir for holding the solution, which is in fluid communication with a needle for delivering the drug, as well as a mechanism for deploying the needle, inserting the needle into the patient, and delivering the dose into the patient.

In a specific embodiment, the kit of the invention is a disposable auto-injector prefilled with the pharmaceutical composition.

Method of Treatment

An embodiment of the invention is a method of improving at least one symptom of a medical condition requiring an adrenergic compound in an individual in need thereof, comprising administering to the individual a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

The composition according to the invention may be employed for any medical condition for which an adrenergic compound, such as epinephrine, is useful. In particular embodiments the adrenergic compound is used for anaphylaxis, cardiac arrest, or asthma, for example.

An embodiment of the invention is a method of treating anaphylaxis in an individual comprising administering to the individual a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

An embodiment of the invention is a liquid pharmaceutical composition for use in improving at least one symptom of a medical condition requiring an adrenergic compound in an individual in need thereof, comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0.

An embodiment of the invention is a use of a liquid pharmaceutical composition comprising an adrenergic compound and at least one antioxidant selected from the group consisting of a bisulfite, a metabisulfite and a sulfite compound, wherein the molar ratio of the adrenergic compound to the at least one antioxidant, measured as sulfite-equivalents, is in the range 1.31-2.20, and wherein the pH of said liquid composition is in the range of about 2.0-5.0, for the manufacture of a medicament for treating anaphylaxis in an individual.

EXAMPLES

Example 1

The following formulation was prepared.

| Ingredient | Amount (mg/ml) |
| --- | --- |
| Epinephrine acid tartrate | 2.0 |
| Sodium chloride | 6.0 |
| Sodium metabisulfite | 0.57 |
| HCl/NaOH | q.s. pH 3.4 |
| Water for injection | q.s. 1.0 ml |

Half the final volume of stock solution (1.2% sodium chloride) was pipetted into a glass beaker, the sodium metabisulfite was added and stirred gently to dissolve. Epinephrine acid tartrate was added and the solution stirred gently to dissolve and mix and the pH adjusted, if required, to 3.4±0.2. The solution was made to volume with degassed water for injection and the solution stirred gently for 10 minutes to mix.

Example 2

Stability Testing of Different Ratios of Metabisulfite:Epinephrine

A 1.1 mg/ml solution of adrenaline ($6.004 \times 10^{-3}$ M), in the form of the tartrate, pH 3.4 and containing 0.6% sodium chloride was used. A range of metabisulfite antioxidant concentrations, with and without admixture of 0.25% di-sodium edetate as chelating agent were tested. The metabisulfite/adrenaline molar ratios tested were 0.1, 0.2, 0.5, 1.0 and 1.5, which correspond to sulfite/adrenaline ratios of 0.2, 0.4, 1.0, 2.0 and 3.0, respectively. For the ease of reference to the general description and claims of this specification, the said values correspond to a molar ratio of adrenaline to sulfite of 5.0, 2.5, 1.0, 0.5 and 0.33, respectively.

The accelerated test temperature was 60° C., protected from light, and samples were pulled at 0, 7, 14, 21 and 28 days. At each pull point, the appearance of the test solution was assessed, the pH measured and the solution assayed for adrenaline content. The appearance of degradation products was noted as area %.

Figure 1:
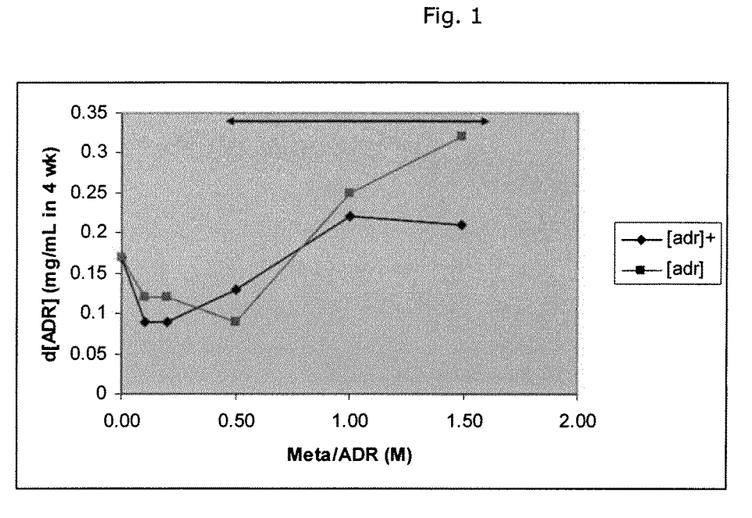
FIG. 1 is a graph illustrating the change in epinephrine contents over four weeks storage at 60° C. against metabisulfite/epinephrine molar ratio.
Figure 2:
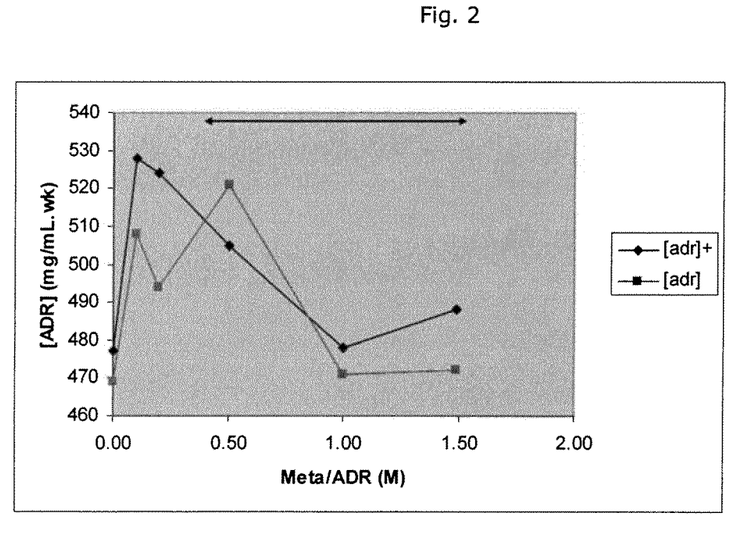
FIG. 2 is a graph illustrating the sum of epinephrine contents over four weeks storage at 60° C. against metabisulfite/epinephrine molar ratio.
Figure 3:
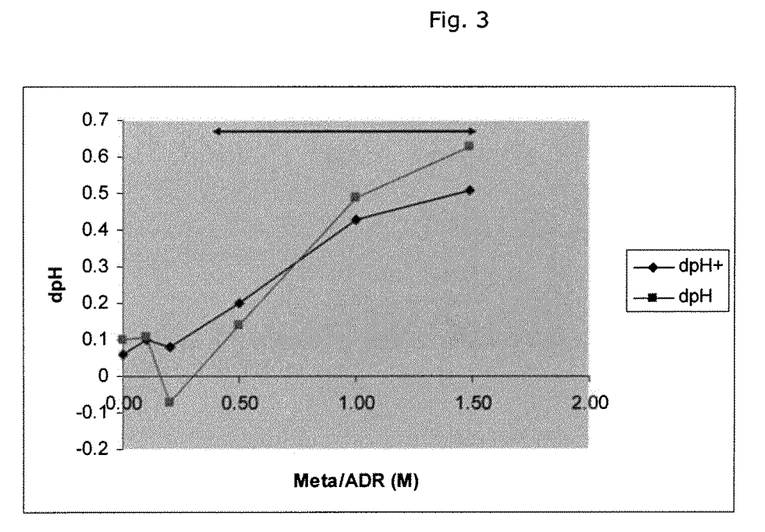
FIG. 3 is a graph illustrating the change in solution pH over four weeks storage at 60° C. against metabisulfite/epinephrine molar ratio.

FIG. 1 shows the difference in adrenaline content, d[ADR], between T=0 and T=4 weeks plotted against the metabisulfite/adrenaline molar ratio. [adr]$^+$ relates to samples containing 0.025% di-sodium edetate, whereas [adr] relates to samples containing no chelating agent. FIG. 2 shows the sum of adrenaline contents over four weeks storage at 60° C. against the metabisulfite/adrenaline molar ratio. FIG. 3 shows the change in solution pH between T=0 and T=4 weeks plotted against metabisulfite/adrenaline molar ratio. dpH$^+$ relates to samples containing 0.025% di-sodium edetate, whereas dpH relates to samples containing no chelating agent.

It appears from FIGS. 1, 2 and 3 that there is a break or a minimum which occurred at a metabisulfite/adrenaline molar ratio less than or equal to 0.5. A molar ratio of 0.5 for metabisulfite/adrenaline corresponds to a molar ratio of 1.0 for sulfite/adrenaline, since two moles of sulfite ion—the actual antioxidant species—is generated per mole of sodium metabisulfite. There was in other words an optimum metabisulfite/adrenaline molar ratio, for adrenaline solution stability to the 60° C. challenge. In addition, above this ratio, at higher metabisulfite concentrations, the increase in pH over the four week storage period was directly related to metabisulfite concentration.

The results reported here indicate two mechanisms; at low (metabisulfite/adrenaline molar ratio≤0.5) metabisulfite concentrations where solution pH and adrenaline were stable but the tendency to (presumed) adrenochrome formation was greater and at high (metabisulfite/adrenaline molar ratio>0.5) metabisulfite concentrations where solution pH increased, adrenaline content decreased and where there was no (presumed) adrenochrome formation.

It is interesting to consider the likely reactions involving metabisulfite in solution. In water sodium metabisulfite dissociates to sodium and sulfite ion.

Sulphite ion reduces carbonyl and alcohol groups and the likely structure of the epinephrine sulphonic acid (ESA) complex, 1-(3,4-dihydroxyphenyl)-methyl-amino-methanesulphonic acid is as shown.

The consumption of sulfite ion should increase pH, which was observed here. It should be noted that there are two moles of sulphite ion generated per mole of sodium metabisulfite. Thus the various plots showing e.g. a metabisulfite:adrenaline molar ratio close to 0.5 can also be interpreted as a sulfite:adrenaline molar ratio of close to 1. This latter ratio is arguably more relevant since it is based on the concentration of the actual anti-oxidant species and the species involved in ESA formation.

At the metabisulfite levels contemplated, there seems to be no advantage in using a chelating agent such as di-sodium edetate.

Example 3

Further Stability Testing of Different Ratios of Metabisulfite:Epinephrine

The below tests disclose more information regarding the optimum molar ratio of sodium metabisulfite to adrenaline for stability of the latter.

The formulation solutions were prepared at a level of 1.0 mg/ml adrenaline (in the form of the tartrate), pH 3.4 containing, 0.6% sodium chloride, with various molar ratios (0.25-0.59) of sodium metabisulfite added. The metabisulfite/adrenaline molar ratios tested were 0.25, 0.34, 0.42, 0.5 and 0.59, which correspond to sulfite/adrenaline ratios of 0.5, 0.68, 0.84, 1.0 and 1.18, respectively. For the ease of reference to the general description and claims of this specification, the said values correspond to a molar ratio of adrenaline to sulfite of 2.0, 1.47, 1.19, 1.0 and 0.85, respectively.

Each sample solution was split into two lots. For each sample solution, one lot was placed at the accelerated test temperature of 60° C., protected from light and the other lot placed in a photo-stability cabinet at 25° C. which provided 13400 lux visible light, 1.50 W.h/m$^2$ UV. Samples were pulled from both conditions at 0, 7, 14 and 28 days At each pull point, the appearance of the test solution was assessed, the pH measured and the adrenaline content measured together with impurities.

Figure 4:
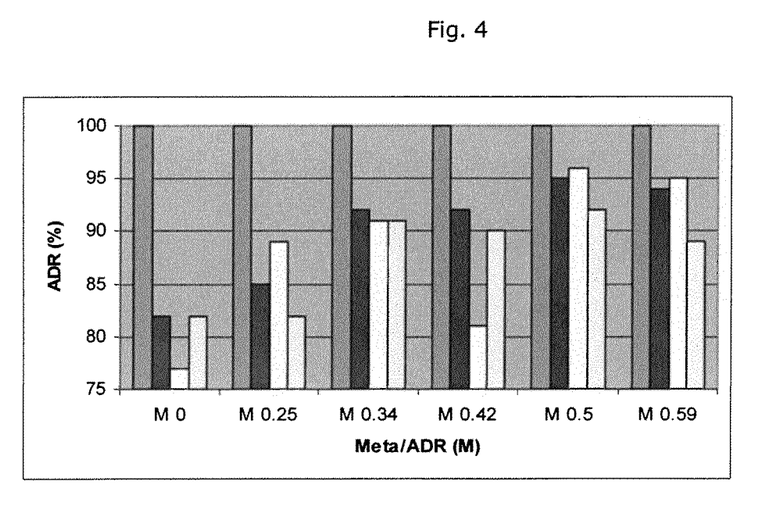
FIG. 4 is a diagram illustrating the change in adrenaline contents during thermal stress at 60° C. at different metabisulfite/epinephrine molar ratios for each of the weeks 0, 1, 2, and 4.
Figure 5:
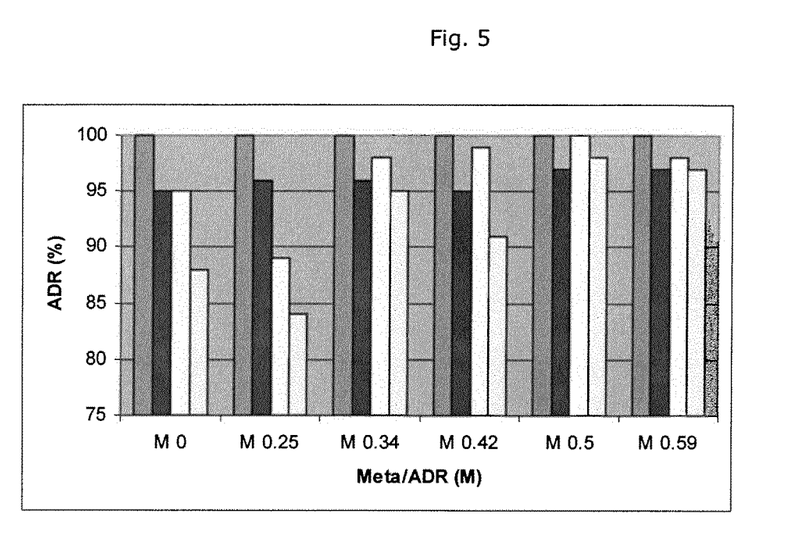
FIG. 5 is a diagram illustrating the change in adrenaline contents during photo-stress at 60° C. at different metabisulfite/epinephrine molar ratios for each of the weeks 0, 1, 2, and 4.

FIG. 4 shows the adrenaline content, relative to T=0, during thermal stress at 60° C., whereas FIG. 5 shows the adrenaline content, relative to T=0, during photo-stress.

The protective effects of metabisulfite against loss of adrenaline, caused by either stress, can be clearly seen. Considering both stresses, the first choice of metabisulfite content, based on the ratios studied here was a half molar with respect to adrenaline. Also, it may be seen that the stability of adrenaline is improved in the molar ratio of metabisulfite to adrenaline in all of the tested range of 0.25 to 0.59.

Figure 6:
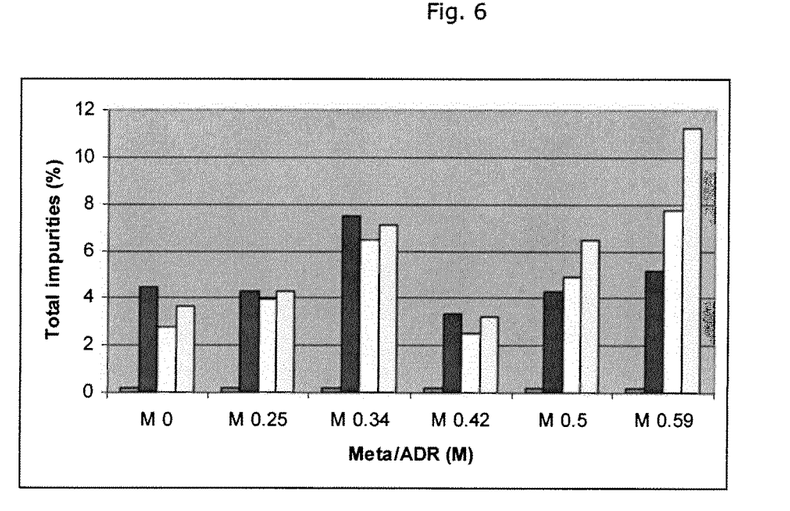
FIG. 6 is a diagram illustrating the change in total impurities contents during thermal stress at 60° C. at different metabisulfite/epinephrine molar ratios for each of the weeks 0, 1, 2, and 4.
Figure 7:
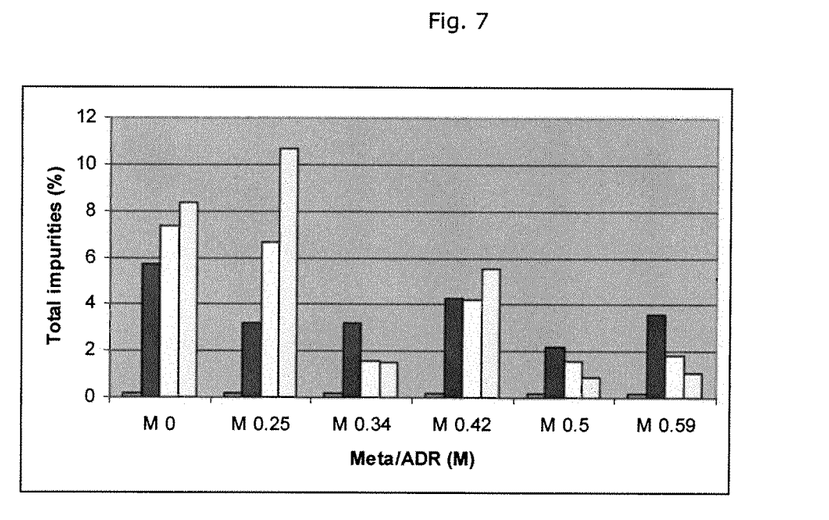
FIG. 7 is a diagram illustrating the change in total impurities contents during photo-stress at 60° C. at different metabisulfite/epinephrine molar ratios for each of the weeks 0, 1, 2, and 4.

FIG. 6 shows the total impurities content, i.e. the contents of degradation products, during thermal stress at 60° C., whereas FIG. 7 shows the total impurities content during photo-stress.

The results for impurities content in the photo-stressed samples were in good agreement with those for the corresponding loss of adrenaline in that the time dependent increase in the content of impurities at low metabisulfite contents mirrored, at least qualitatively, the time dependent adrenaline loss.

For heat stressed samples, a correlation between adrenaline loss and the appearance of impurities was less obvious. Heat stressed samples with no anti-oxidant had amongst the lowest levels of total impurities but the greatest loss of adrenaline and the highest level of total impurities was in M 0.59, a sample which exhibited one of the lowest adrenaline losses on storage.

On the basis of total impurities from heat stress the best metabisulfite:adrenaline ratio was 0.42 and on the basis of total impurities from photo-stress, 0.5.

Figure 8:
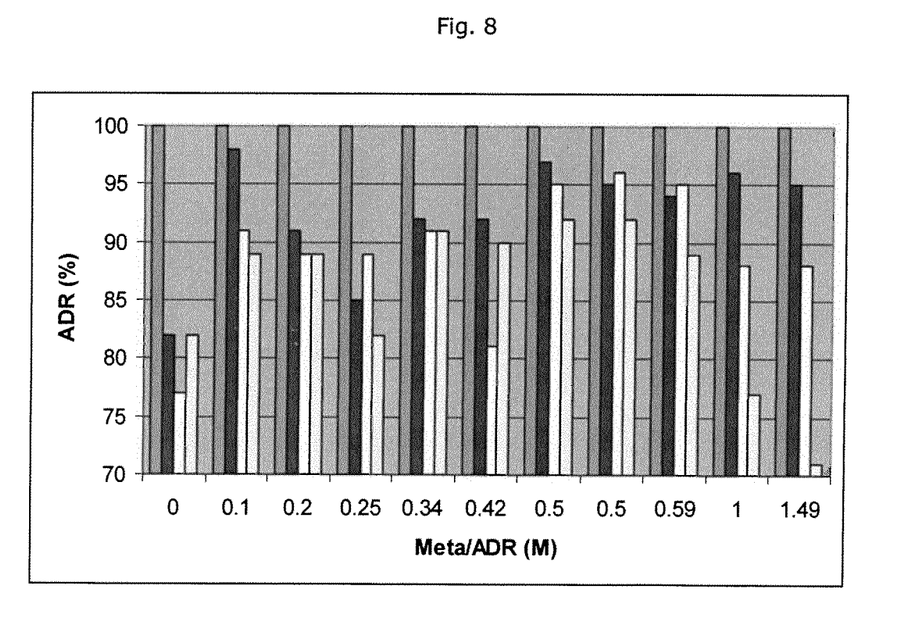
FIG. 8 is a diagram illustrating the change in adrenaline contents during thermal stress at 60° C. at different metabisulfite/epinephrine molar ratios for each of the weeks 0, 1, 2, and 4.
Figure 9:
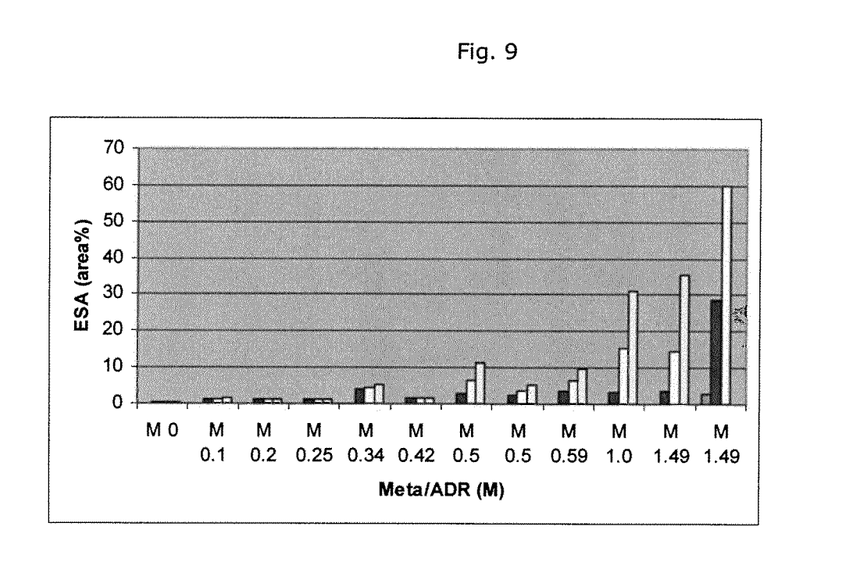
FIG. 9 is a diagram illustrating the formation of epinephrine sulfonic acid (ESA) at 60° C. at different metabisulfite/epinephrine molar ratios for each of the weeks 0, 1, 2, and 4.

FIG. 8 summarises the results disclosed in Examples 2 and 3 and shows the adrenaline content, relative to T=0, during thermal stress at 60° C. FIG. 9 shows the formation of epinephrine sulfonic acid (ESA), one of the major degradation products of adrenaline/epinephrine, at 60° C. at different metabisulfite:adrenaline molar ratios.

FIGS. 8 and 9 clearly show the deleterious effects of high metabisulfite concentrations. Of course, since in solution, two moles of sulfite ion, the actual anti-oxidant species and the species involved in ESA formation, are generated per mole of sodium metabisulfite, it would appear that what is important is the underlying sulfite:adrenaline ratio which was found to have an optimum value of about 1.0.

The invention claimed is:

1. A liquid pharmaceutical composition comprising an adrenergic compound and at least one antioxidant that is a member selected from the group consisting of a bisulfite and, a metabisulfite, wherein the molar ratio of the adrenergic compound to the at least one antioxidant, measured as sulfite-equivalents, is 1.31-2.20, and wherein the pH of said liquid composition is between about pH 2.0-4.0.

2. The pharmaceutical composition according to claim 1, wherein the adrenergic compound is a member selected from the group consisting of epinephrine, norepinephrine, phenylephrine, α-methylnorepinephrine, dopamine, methoxamine, dobutamine, prenalterol, isoproterenol, fenoterol, albuterol, terbutaline, metaproterenol, and physiologically acceptable salts thereof.

3. The pharmaceutical composition according to claim 1, wherein the adrenergic compound is a member selected from the group consisting of epinephrine, norepinephrine, isoproterenol and dopamine, and physiologically acceptable salts thereof.

4. The pharmaceutical composition according to claim 1, wherein the adrenergic compound is epinephrine or a physiologically acceptable salt thereof.

5. The pharmaceutical composition according to claim 1, wherein the antioxidant is sodium metabisulfite.

6. The pharmaceutical composition according to claim 1, wherein the molar ratio of the at least one adrenergic compound to the at least one antioxidant is 1.31 to 2.00.

7. The pharmaceutical composition according to claim 1, having a pH in the range of pH 2.5-4.0.

8. The pharmaceutical composition according to claim 7, wherein the pH is in the range of pH 3.3-3.5.

9. The pharmaceutical composition according to claim 1, further comprising one or more excipients or additives.

10. The pharmaceutical composition according to claim 2, comprising:

| | |
|---|---|
| Epinephrine acid tartrate | 2.0 mg/ml |
| Sodium chloride | 6.0 mg/ml |
| Sodium metabisulfite | 0.57 mg/ml |
| HCl/NaoH | q.s. pH 3.4 |
| Water for injection | q.s. 1.0 ml. |

11. A method for stabilizing a liquid pharmaceutical composition comprising an adrenergic compound, comprising the steps of i) providing a solution of an adrenergic compound, ii) adding at least one antioxidant selected from the group consisting of a bisulfite, and a metabisulfite, iii) adjusting the pH of the composition to a value in the range of pH 2.0-4.0 optionally by addition of an acid or a base, wherein the molar ratio of the adrenergic compound to the at least one antioxidant, measured as sulfite-equivalents, is in the range of 1.31-2.20.

12. A kit comprising:
v) a liquid pharmaceutical composition comprising an adrenergic compound and at least one antioxidant selected from the group consisting of a bisulfite, and a metabisulfite, wherein the molar ratio of the adrenergic compound to the at least one antioxidant, measured as sulfite-equivalents, is in the range of 1.31-2.20, and wherein the pH of said liquid composition is in the range of about 2.0-4.0, and
vi) an administration device.

13. The kit according to claim 12 wherein the administration device is an ampoule or an auto-injector.

14. A method of improving at least one symptom of a medical condition requiring an adrenergic compound in an individual in need thereof, comprising administering to the individual a liquid pharmaceutical composition comprising an adrenergic compound and at least one antioxidant that is a member selected from the group consisting of a bisulfite, and a metabisulfite, wherein the molar ratio of the adrenergic compound to the at least one antioxidant, measured as sulfite-equivalents, is 1.31-2.20, and wherein the pH of said liquid composition is in the range of about pH 2.0-4.0.

15. A method of treating anaphylaxis in an individual comprising administering to the individual a liquid pharmaceutical composition comprising an adrenergic compound and at least one antioxidant member selected from the group consisting of a bisulfite, and a metabisulfite, wherein the molar ratio of the adrenergic compound to the at least one antioxidant, measured as sulfite-equivalents, is 1.31-2.20, and wherein the pH of said liquid composition is in the range of about pH 2.0-4.0.

16. A liquid pharmaceutical composition for use in improving at least one symptom of a medical condition requiring an adrenergic compound in an individual in need thereof, comprising an adrenergic compound and at least one antioxidant selected from the group consisting of a bisulfite, and a metabisulfite, wherein the molar ratio of the adrenergic compound to the at least one antioxidant, measured as sulfite-equivalents, is 1.31-2.20, and wherein the pH of said liquid composition is in the range of about pH 2.0-4.0.

* * * * *

UNITED STATES PATENT AND TRADEMARK OFFICE
CERTIFICATE OF CORRECTION

PATENT NO.       : 8,628,805 B2                                              Page 1 of 1
APPLICATION NO.  : 12/794163
DATED            : January 14, 2014
INVENTOR(S)      : Baillie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Thirtieth Day of May, 2017

Michelle K. Lee
*Director of the United States Patent and Trademark Office*